United States Patent [19]

Miike

[11] Patent Number: 5,665,606
[45] Date of Patent: Sep. 9, 1997

[54] METHOD FOR ASSAYING A SUBSTANCE USING A POLYACRIDINIUM COMPOUND

[75] Inventor: Akira Miike, Sunto-gun, Japan

[73] Assignee: Kyowa Medex Co., Ltd., Tokyo, Japan

[21] Appl. No.: 420,316

[22] Filed: Apr. 10, 1995

[30] Foreign Application Priority Data

Apr. 11, 1994 [JP] Japan .................... 6-072066

[51] Int. Cl.$^6$ .............. G01N 33/533; G01N 33/544; G01N 33/574; G01N 33/577
[52] U.S. Cl. .................. 436/526; 436/531; 436/546; 436/800; 436/813; 436/817; 530/391.3
[58] Field of Search .................. 436/526, 817, 436/800, 813, 546, 531; 530/391.3

[56] References Cited

U.S. PATENT DOCUMENTS

| | | | |
|---|---|---|---|
| 4,745,181 | 5/1988 | Law et al. | 530/387 |
| 4,761,382 | 8/1988 | Woodhead et al. | 436/536 |
| 4,918,192 | 4/1990 | Law et al. | 546/104 |
| 5,032,381 | 7/1991 | Bronstein et al. | 435/7.21 |
| 5,110,932 | 5/1992 | Law et al. | 546/102 |

FOREIGN PATENT DOCUMENTS

| | | |
|---|---|---|
| 534380 | 3/1993 | European Pat. Off. |
| WO92-05281 | 4/1992 | WIPO |

OTHER PUBLICATIONS

J. Voyta, Chemical Abstract of French patent No. 2,649,205, published 1991.

A. Baret, Chemical Abstract of European patent No. 256, 932, published 1988.

Abstract of World Patent PCT 92–05281, published Apr. 2, 1992.

English abstract (Derwent) of Japanese Patent 52–55263 published Mar. 10, 1992.

*Primary Examiner*—Mary E. Ceperley
*Attorney, Agent, or Firm*—Fitzpatrick, Cella, Harper & Scinto

[57] ABSTRACT

The present invention provides a new analytical method that an antigen, an antibody or a nucleic acid can be assayed at a high sensitivity in the immunoassay.

The present invention provides a method for assaying a substance which comprises the steps of (a) reacting an antigen, an antibody or a nucleic acid which is the substance to be measured with an antibody, an antigen or a nucleic acid to which a polyacridinium compound is bound and which can be bound to the substance to be measured, (b) carrying out a luminescence treatment, and (c) measuring the luminescent intensity of the reaction solution.

1 Claim, No Drawings

METHOD FOR ASSAYING A SUBSTANCE USING A POLYACRIDINIUM COMPOUND

BACKGROUND OF THE INVENTION

This invention relates to a method for assaying an antigen, an antibody or a nucleic acid at a high sensitivity using polyacridinium.

Luciferase catalyzes a luminescent reaction and this enzyme has been used in the immuno-diagnosis. However, the luciferase adheres to an instrument such as the tube wall, and it is difficult to perform the accurate analysis.

In contrast, when an acridinium compound, which is a chemical luminescent substance, is used in the immuno-diagnosis, the acridinium compound does not adhere to an instrument. Therefore, it can be easily applied to labeling, and has a good luminous efficiency [EP103469A (U.S. Pat. No. 4,761,382), EP263657A (U.S. Pat. Nos. 4,745,181, 4,918,192, 5,110,932), Japanese Laid-Open Patent Application H05-255263].

However, when an acridinium compound is used as a marker in the immuno-diagnosis, only one molecule of the acridinium compound can be bound to one amino group of an antibody or an antigen. Thus, the amount of the acridinium compound bound to the antibody or the antigen is not enough, it is impossible to obtain a sufficient amount of luminescence.

The present invention is based on our new finding that, when the polyacridinium compound can be bound to the antibody or the antigen, it can be used as a marker in the immunoassay, and a large number of the acridinium compound can be bound to one molecule of the antibody or the antigen, and consequently, one molecule of the antibody or the antigen binds to a marker having a very strong luminescent intensity.

The present invention provides a method for assaying an antigen, an antibody or a nucleic acid at an ultra-high sensitivity using a polyacridinium compound.

SUMMARY OF THE INVENTION

This invention relates to a method for assaying a substance which comprises the steps of (a) reacting an antigen, an antibody or a nucleic acid which is a substance to be measured with an antibody, an antigen or a nucleic acid to which a polyacridinium compound is bound and which can be bound to the substance to be measured, (b) carrying out a luminescence treatment, and (c) measuring a luminescent intensity of the reaction solution.

DETAILED DESCRIPTION OF THE INVENTION

The polyacridinium compound used in this invention may be any polyacridinium compound which is obtained from a homopolymer of an acridine derivative having an olefin in the terminal or from a copolymer of the acridine derivative with maleic anhydride or a maleic acid derivative. Preferably, the polyacridinium compound used in this invention is a compound represented by formula (I):

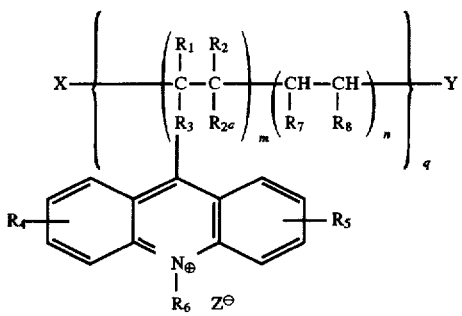

[wherein:

m is an optionally changeable positive integer of 1 to 10,000, n is an optionally changeable positive integer of 0 to 10,000, q is a positive integer of m+n, X denotes hydrogen or a lower alkyl, Y denotes hydrogen, a lower alkyl or a metal, $R_1$, $R_2$ and $R_{2a}$ are the same or different and each denotes hydrogen, a lower alkyl, a lower alkanoyl, a substituted or unsubstituted aroyl, carboxyl or cyano, $R_3$ denotes a group represented by the formula —[COO]$_s$—W—[OCO]$_p$—, —[COO]$_s$—W—N($R_9$)CO—, —COO—W—$W_a$—[N($R_9$)CO]$_p$—, or —CON($R_9$)—W—[N($R_{9a}$)CO]$_p$— (in which W and $W_a$ are different and each denotes alkylene, methylene, a substituted or unsubstituted phenylene, or a substituted or unsubstituted naphthylene, $R_9$ and $R_{9a}$ are the same or different and each denotes hydrogen, a lower alkylsulfonyl, or a substituted or unsubstituted arylsulfonyl, and s and p are the same or different and each denotes an integer of 0 or 1), $R_4$ and $R_5$ are the same or different and each denotes hydrogen, a lower alkyl, a lower alkoxy, carboxyl or sulfo, $R_6$ denotes a substituted or unsubstituted lower alkyl, $R_7$ denotes carboxyl, lower alkoxycarbonyl,

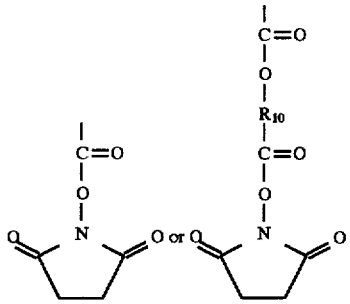

(in which $R_{10}$ denotes alkylene, a substituted or unsubstituted phenylene, or a substituted or unsubstituted naphthylene), and $R_8$ denotes carboxyl, lower alkoxycarbonyl, a substituted or unsubstituted alkyl, or a substituted or unsubstituted aryl, or $R_7$ and $R_8$ together form a group represented by the formula

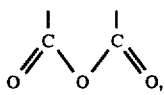

and

Z denotes halogen, methanesulfonyloxy or trifluoromethanesulfonyloxy.

In the definitions of the groups of formula (I), the optional integer indicated by m is 1 to 10,000, preferably 1 to 1,000. The optional integer indicated by n is 0 to 10,000, preferably 1 to 10,000, especially preferably 0 to 1,000, more preferably 1 to 1,000. q is 1 to 20,000, preferably 1 to 2,000.

Examples of lower alkyl and the alkyl group in lower alkanoyl, lower alkoxy and lower alkylsulfonyl are linear or branched alkyl groups having 1 to 6 carbon atoms such as methyl, ethyl, propyl, isopropyl, butyl, isobutyl, tert-butyl, pentyl and hexyl. Substituents of the substituted lower alkyl are the same or different, and the number of the substituents per nucleus is from 1 to 3. Examples of the substituents of the lower alkyl include sulfo, carboxyl and hydroxyl.

Examples of alkylene are alkylene groups having 1 to 10 carbon atoms such as methylene, ethylene, trimethylene, propylene, tetramethylene, ethylethylene, pentamethylene, hexamethylene and octamethylene.

Examples of aryl and the aryl group in arylsulfonyl and aroyl include phenyl and naphthyl. Substituents in the aromatic ring of the substituted aryl, substituted arylsulfonyl, substituted phenylene and substituted naphthylene are the same or different, and the number of the substituents per nucleus is from 1 to 3. Examples of the substituents of these group include lower alkyl, hydroxy, halogen, lower alkoxy, sulfo and carboxyl. Examples of halogen include chlorine, bromine, iodine and fluorine. Examples of lower alkyl and the alkyl group in lower alkoxy are the same as defined above. Examples of the metal include lithium, sodium, potassium and aluminum.

The compound represented by formula (I) is hereinafter referred to as Compound (I). This is the same as other compounds.

A process for producing Compound (I) used in this invention is described below.

Compound (I) can be obtained by the following process based on "Jikken Kagaku Koza (Course of Experimental Chemistry)", 4th edition, compiled by Chemical Society of Japan, No. 22, Organic Synthesis IV, p. 120, published by Maruzen, 1992, and —ibid— No. 22, Synthesis of Polymers, p. 116, published by Maruzen, 1992.

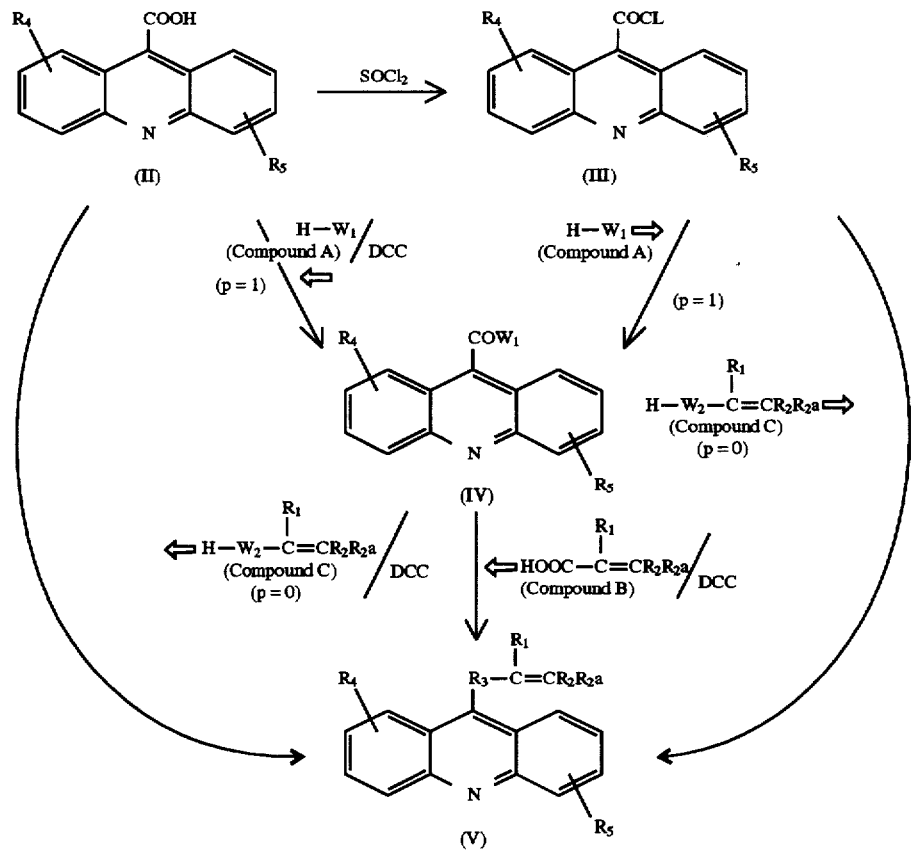

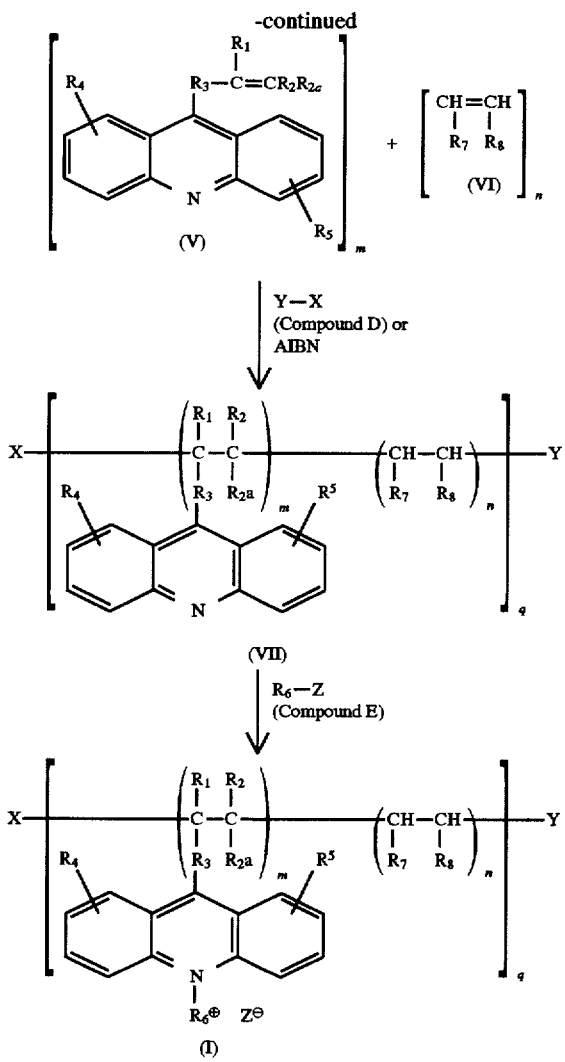

[wherein:

$W_1$ denotes O—W—OH, O—W—N(R$_9$)H, O—W—W$_a$—N(R$_9$)H or N(R$_9$)—W—N(R$_{9a}$)H, $W_2$ denotes HO—W, HO—W—W$_a$ or HN(R$_9$)—W, and W, W$_a$, m, n, s, q, R$_1$, R$_2$, R$_{2a}$, R$_3$, R$_4$, R$_5$, R$_6$, R$_7$, R$_8$, R$_9$, X, Y and Z are the same as defined above].

Compound (I) can be obtained by copolymerizing the acridine derivative (V) with a lactic acid derivative (VI).

Compound (V) in which p of R$_3$ is 1 can be obtained by the following method.

Compound (IV) can be obtained by reacting Compound (II) with Compound (A) in the presence of dicyclohexylcarbodiimide (DCC). The reaction is carried out at 4° to 110° C. for 1 to 12 hours.

Examples of a solvent used in the reaction include dioxane, tetrahydrofuran, benzene, toluene, acetonitrile, chloroform, 1,2-dichloroethane and N,N'-dimethylformamide.

Compound (III) can be obtained by reacting Compound (II) with thionyl chloride. The reaction is carried out at 0° to 110° C. for 1 to 6 hours.

Examples of a solvent used in the reaction include dioxane, tetrahydrofuran, benzene, toluene, acetonitrile, chloroform and 1,2-dichloroethane.

Compound (IV) can be obtained by reacting Compound (III) with Compound (A). The reaction is carried out at 0° to 110° C. for 1 to 6 hours.

Examples of the solvent used in the reaction are the same as mentioned above. The reaction may be carried out in the presence of a base such as pyridine, triethylamine, N-methylmorphorine and dimethylaminopyridine.

Compound (V) can be obtained by reacting Compound (IV) with Compound (B) in the presence of DCC. The reaction can be carried out under the above-mentioned reaction conditions.

Compound (V) in which p is 0 [Compound (V)p$_o$] can be obtained by reacting Compound (II) with Compound (C) in the presence of DCC. Alternatively, Compound (V)p$_o$ can be obtained by reacting Compound (III) with Compound (C) under the above-mentioned reaction conditions. Compound (V) in which R$_9$ and R$_{9a}$ are alkyl or arylsulfonyl can be obtained by reacting a compound corresponding to Compound (V) in which R$_9$ and R$_{9a}$ are hydrogens with an alkyl halide or an arylsulfonyl halide. The reaction is carried out at 0° to 110° C. for 1 to 24 hours.

Examples of the solvent used in the reaction include tetrahydrofuran, dioxane, benzene, toluene, acetonitrile, chloroform, 1,2-dichloroethane and N,N'-dimethylformamide. The reaction may be carried out in the presence of a base, if required, as mentioned above.

Compound (VII) can be obtained from Compound (V) alone or by reacting Compound (V) with Compound (VI) in the presence of a polymerization initiator such as Compound (D) and azoisobutyronitrile (AIBN) and in the presence or absence of a solvent. The reaction is terminated with the addition of a reaction terminator such as isopropanol.

Examples of the solvent include cyclohexane, heptane, hexane, toluene and benzene. These solvents may be used either singly or in combination. The reaction is carried out at −80° to 20° C. for 0.1 to 6 hours.

When maleic anhydride is used as Compound (VI), a maleic acid ester compound can be obtained by reacting the obtained Compound (VII) with Compound (F) or Compound (G) represented by the following formula:

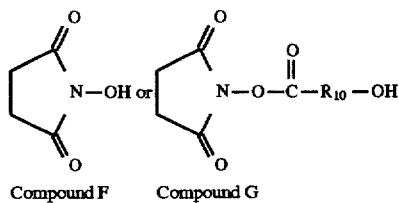

(wherein $R_{10}$ is the same as defined above).

Compound (VII) is reacted with Compound (F) or Compound (G) in the presence or absence of a solvent obtain the maleic acid ester compound. The reaction is carried out at 0° to 60° C. for 1 to 24 hours. Examples of the solvent include dioxane, tetrahydrofuran, benzene, toluene, acetonitrile, chloroform and 1,2-dichloroethane.

The copolymerization reaction can be carried out using Compound (VIII) instead of Compound (VI). The Compound (VIII) [Compound (VIIIa) or Compound (VIIIb)] is obtained from maleic anhydride and Compound (F) or Compound (G).

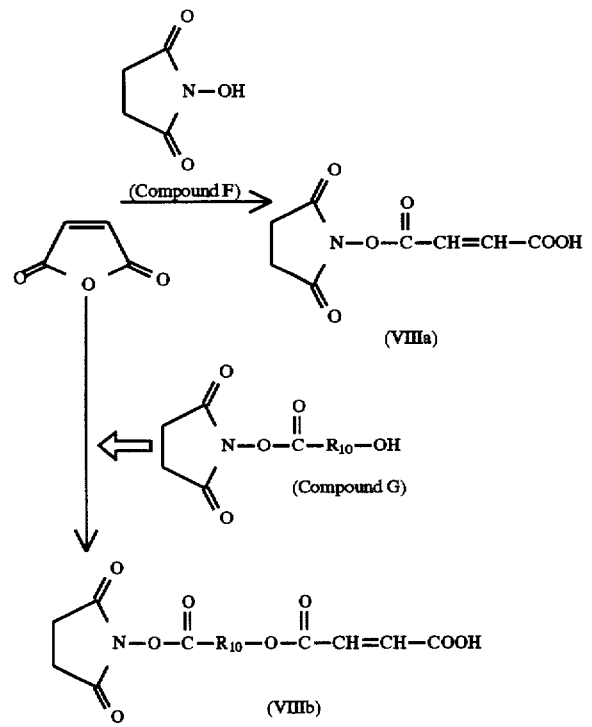

(wherein $R_{10}$ is the same as defined above).

Compound (VIII) can be obtained by reacting Compound (VII) with Compound (F) or Compound (G) under the above-mentioned reaction conditions.

Compound (I) can be obtained by reacting Compound (VII) with Compound (E) in the presence or absence of a solvent. The reaction is carried out at 0° to 60° C. for 1 to 24 hours.

Examples of a solvent used in the reaction include dioxane, tetrahydrofuran, benzene and toluene.

The intermediate and the desired compound obtained in the above-mentioned method can be isolated and purified by a purification method conventionally used in organic synthesis chemistry such as filtration, extraction, washing, drying, concentration, recrystallization, various types of chromatography. It is also possible to subject the intermediate to the subsequent reaction without purification.

Specific examples of the polyacridinium compound used in this invention are shown in Table 1.

TABLE 1-1

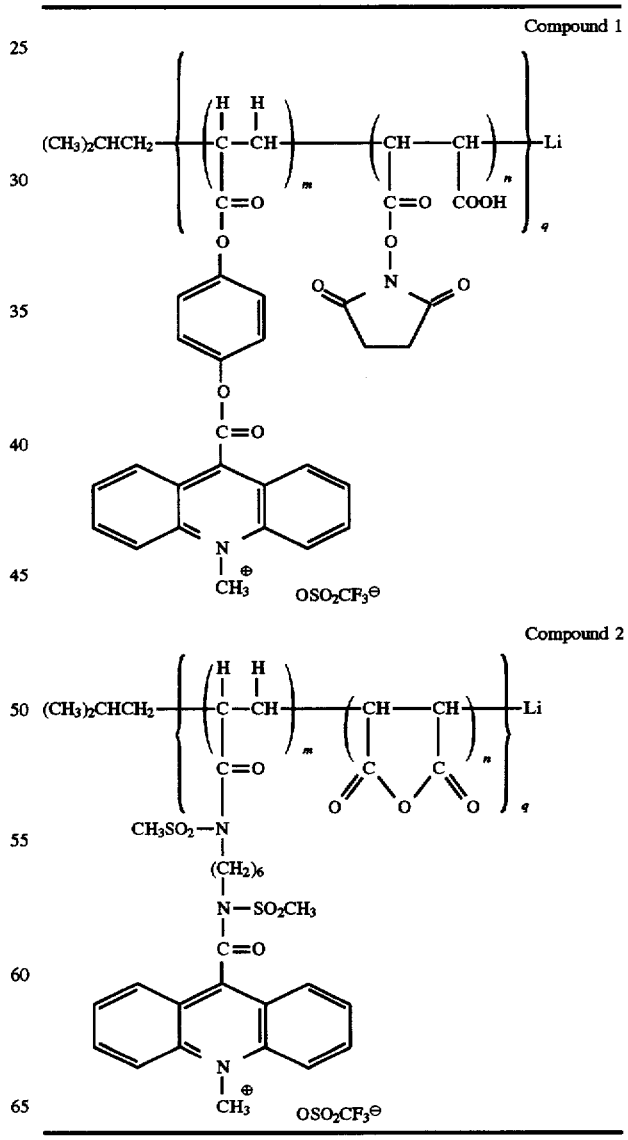

TABLE 1-2
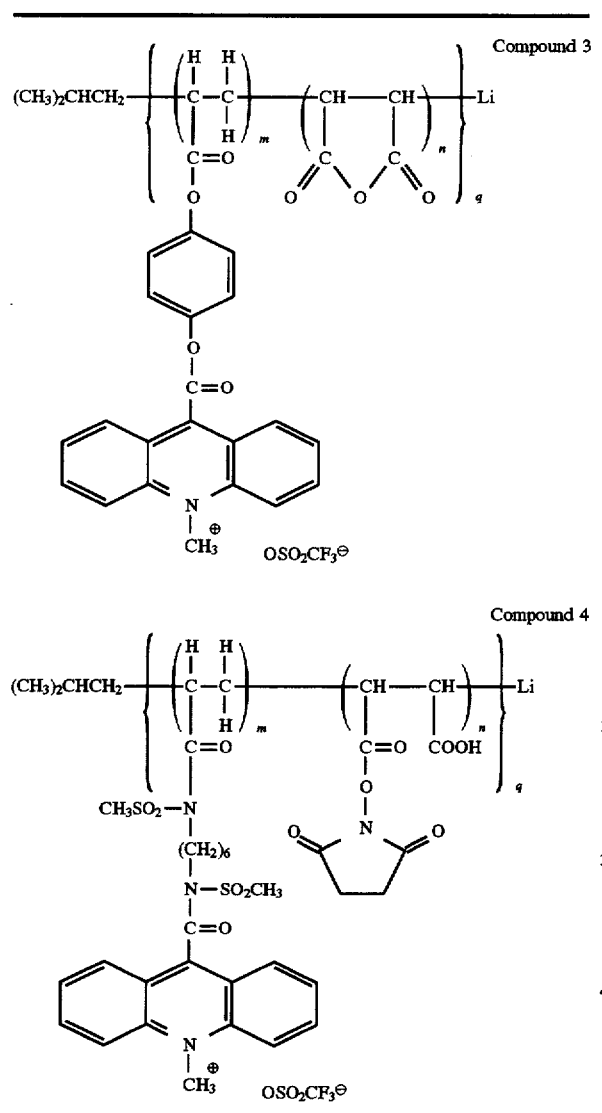
TABLE 1-3
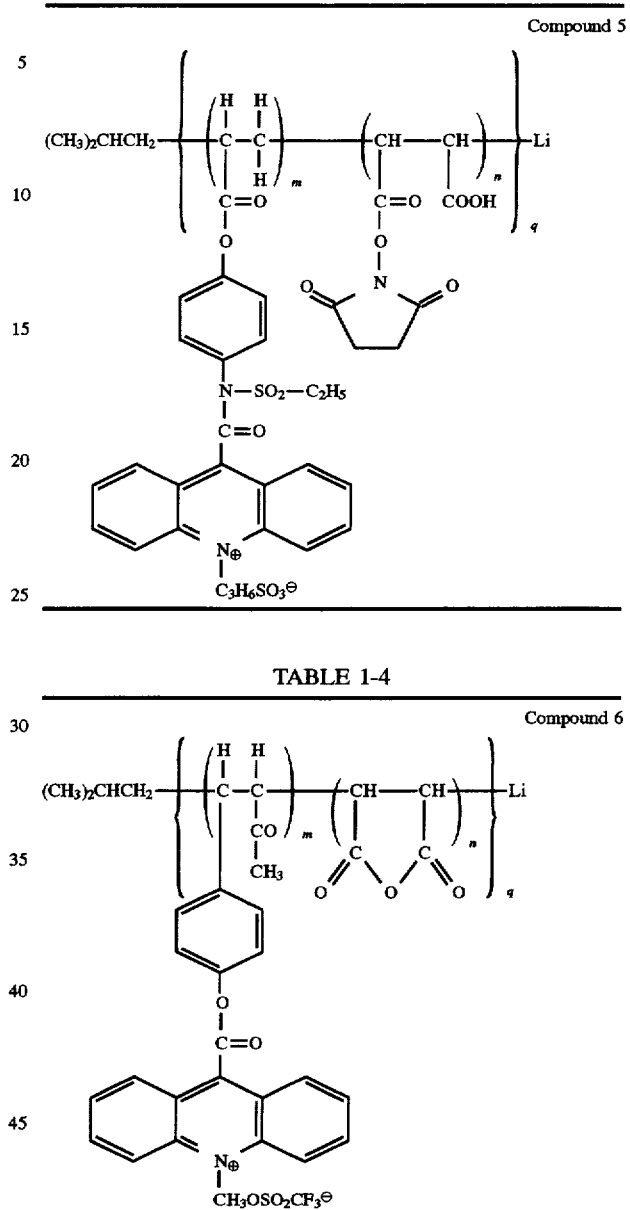
TABLE 1-4
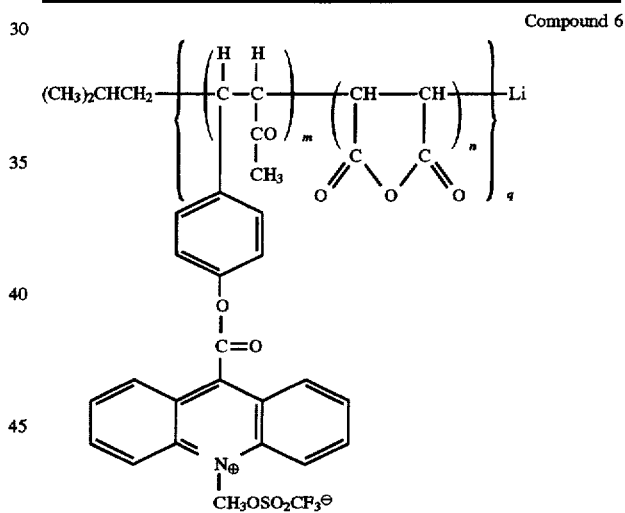

TABLE 1-4-continued

Compound 7

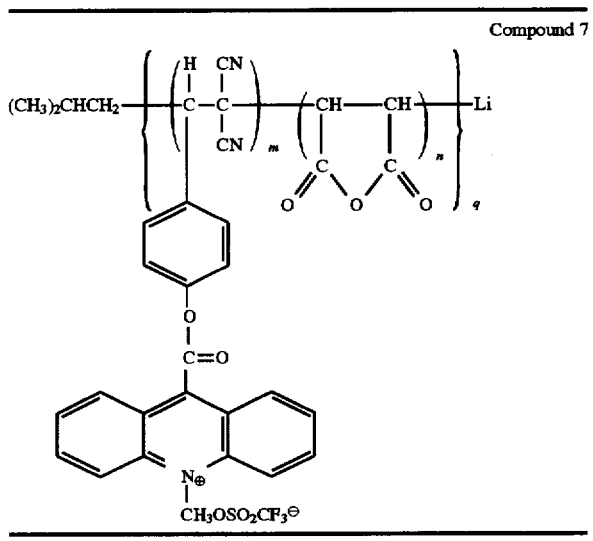

TABLE 1-5

Compound 8

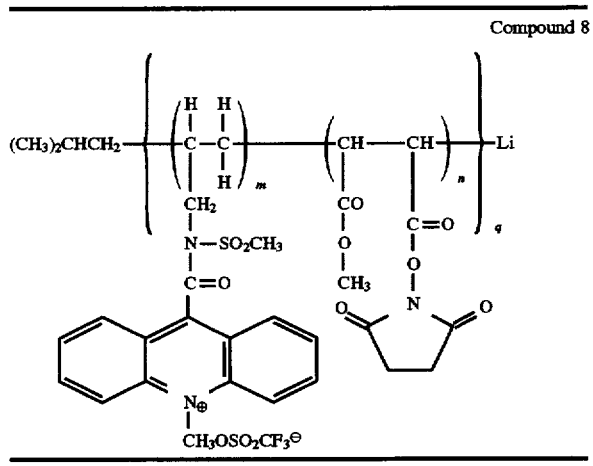

The method for assaying the substance in this invention is described below.

In the method for assaying the substance according to this invention, the antigen is generically a substance that can induce immune response. The antibody is generically a protein that is specifically bound to the antigen. The nucleic acid is, for example, DNA or RNA.

A sandwich method is preferably used in immunoassay of this invention. The basis of the sandwich method is as follows. (1) A substance to be measured in a sample is bound to an antigen, an antibody or a nucleic acid which is bound to a carrier (immobilized phase) and which can be bound to the substance to be measured. (2) Then, the reaction mixture is bound to an antigen, an antibody or a nucleic acid having a polyacridinium compound, preferably Compound (I) [labeling compound]. (3) The reaction mixture of step (2) is subjected to the luminescence treatment. (4) The luminescent intensity of the labeling compound bound to the substance is measured in the immobilized layer. The carrier in the sandwich method is, for example, a carrier conventionally used in the immunoassay such as beads, a 96-well plate and magnetic particles.

The antigen, the antibody or the nucleic acid having the labeling compound (hereinafter referred to as a "labeled substance") can be obtained by uniformly mixing the antigen, the antibody or the nucleic acid, which can be bound to the substance to be measured, with the polyacridinium compound, preferably Compound (I), in a buffer solution (pH 6 to 11) such as a phosphate buffer solution and a tris-hydrochloride buffer solution. The reaction is carried out at 4° to 50° C. for 10 minutes to 72 hours.

The labeled substance, which is a reaction product, can be isolated by an isolation means such as gel chromatography, ion exchange chromatography, affinity chromatography and a high-performance liquid chromatography.

According to the known method, the sample solution containing the substance to be measured is put in contact with the carrier having the antigen, the antibody or the nucleic acid which can be bound to the substance to be measured, in a buffer solution (pH of 5 to 9) such as a phosphate buffer solution, a Good's buffer solution, and a tris-hydrochloride buffer solution. The reaction is carried out at 4° to 40° C. for 1 minute to 72 hours. As the carrier, a carrier conventionally used in immunoassay such as beads, a 96-well plate and magnetic particles is preferable. The obtained reaction mixture is washed with a buffer solution such as a phosphate buffer solution, a Good's buffer solution and a tris-hydrochloride buffer solution. After the completion of the washing, the reaction mixture is put in contact with the above-mentioned labeled substance in a buffer solution such as a phosphate buffer solution, a Good's buffer solution and a tris-hydrochloride buffer solution at 4° to 40° C. for 1 minute to 72 hours. The resulting reaction mixture is washed with a buffer solution such as a phosphate buffer solution, a Good's buffer solution and a tris-hydrochloride buffer solution.

The procedure for the luminescence treatment is as follows. A buffer solution having a pH of 9 or less such as an acetate buffer solution and a phosphate buffer solution containing hydrogen peroxide is added to the reaction mixture for reaction, and the reaction solution is then adjusted to a pH of 7 or more, preferably a pH of 9.0 to 12 with a base such as sodium hydroxide and potassium hydroxide. Then luminescence is generated.

A luminescence intensity of the extracted free acridinium compound is measured by a spectrophotometer at a wave length of 190 to 750 nm, preferably 400 to 600 nm. Thus, it is possible to measure the substance to be measured in the sample. The buffer solution used in the following measurement method may contain a compound conventionally used in the immunoassay such as albumin, $NaN_3$ and a surface-active agent.

This invention will be illustrated by referring to the following Examples.

EXAMPLES

Example 1:
Measurement of a carcinoembryonic antigen (CEA):
(1) Labeling of an Antibody An anti-CEA mouse monoclonal antibody was labeled in accordance with a method described in Clinical Chemistry, vol. 29,No. 8, p. 1474 (1983). To 30 μl of a solution of Compound 1 obtained in Reference Example 1 was added 300 μl of a 0.1-M phosphate buffer solution (pH 8.0) containing 50 μg of the anti-CEA mouse monoclonal antibody. After the labeling reaction was carried out for 10 minutes, 100 μl of a 10 g/l-lysine hydrochloride solution was added to terminate the reaction. The unreacted antibody and polyacridinium compound were removed via column chromatography using Cephadex G-50 (80×6 mm, made by Pharmacia) to obtain a polyacridinium compound-labeled anti-CEA antibody (hereinafter abbreviated as a "poly-labeled antibody").

(2) Labeling of the Anti-CEA Antibody With an Acridinium Ester

For comparison, the anti-CEA mouse monoclonal antibody was labeled with an acridinium derivative-1 represented by the formula:

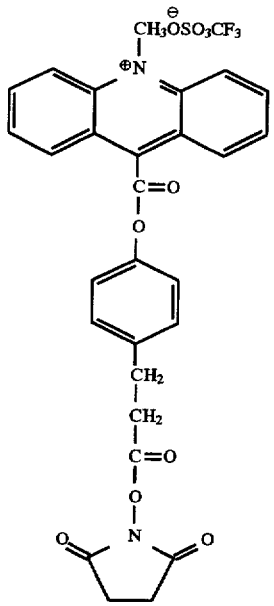

(made by Dojin Kagaku Kenkyusho) as a typical example of the conventional acridinium compound (this antibody is hereinafter abbreviated as a "mono-labeled antibody").

(3) Preparation of a Polystyrene Tube on Which an Anti-CEA Antibody is Immobilized An anti-CEA monoclonal antibody which is different in reactivity from the antibody used for labeling was immobilized on a polystyrene test tube (75×12 mm). To the test tube was added 200 μl of a 10 μg/ml anti-CEA antibody solution dissolved in a 10 mM phosphate buffer solution (pH 8.0), and allowed to stand overnight. After the supernatant solution was removed by suction, 500 μl of a 10 mM phosphate buffer solution (pH 8.0) containing 1% bovine serum albumin (BSA) and 0.1% $NaN_3$ was added to the residue, and the mixture was preserved.

(4) Measurement of CEA

To the polystyrene tube on which the anti-CEA antibody was immobilized were added 50 μl of standard CEA adjusted to 0 to 10.0 ng/ml and 100 μl of the poly-labeled anti-CEA antibody or 100 μl of the mono-labeled anti-CEA antibody, and incubated at room temperature for 1 hour. The reaction solution was taken off through suction, and 1 ml of a 10 mM phosphate buffer solution (pH 8.0) containing 0.05% Tween 20 (made by Wako Pure Chemical Industries, Ltd.) was then added to the residue as a wash liquid. The supernatant was taken off through suction. This process was repeated three times. A 10 -mM acetate buffer containing 0.3% hydrogen peroxide and having a pH of 3 was added to the tube, and 200 μl of an aqueous solution containing 0.1M sodium hydroxide was then added thereto. The luminescence of the resulting reaction solution was measured by Biolumat LB9500T (manufactured by Berthold). The results are shown in Table 2.

According to the above method, CEA concentration in the sample was determined by the immunoassay using the polyacridinium compound (Compound 6 in Reference Example 3, Compound 7 in Reference Example 4 or Compound 8 in Reference Example 5)-labeled antibody. In comparison with mono-labeled antiboty, these poly-labeled antibody exhibit high luminescence. The counts of luminescence using Compound 6, 7 and 8 are 12.5, 7.8 and 24.6 times as much as that of luminescence using mono-acridinium compound, respectively.

TABLE 2

| CEA concentration (ng/ml) | Monolabeled antibody (count) | Poly-labeled antibody (count) |
| --- | --- | --- |
| 0 | 2751 | 5481 |
| 1.0 | 9547 | 265478 |
| 2.0 | 16328 | 531491 |
| 5.0 | 36759 | 1326174 |
| 10.0 | 70899 | 2652604 |

Example 2:

The sera of three persons were used as test samples, and the concentration of CEA in the sera was measured in the same manner as in Example 1. For reference, the concentration of CEA in the same test samples was measured by enzyme immunoassay [CEA-EIA one-step kit (made by Abbott Laboratories)]. The results are shown in Table 3.

TABLE 3

| | Enzyme immunoassay (ng/ml) | Present method (ng/ml) |
| --- | --- | --- |
| Specimen 1 | 1.3 | 1.32 |
| Specimen 2 | 5.7 | 5.71 |
| Specimen 3 | 12.8 | 13.0 |

Example 3:

The measurement limit in the lower concentration when CEA was assayed by the method of this invention or the method using the mono-labeled antibody was measured by the following method. The sera of healthy persons whose CEA concentrations had been already known were diluted stepwise in a 10-fold dilution series. The samples containing the diluted CEA and containing the dilute alone (control) were measured five times by the method described in Example 1. When there is a significant difference (level of significance 1% or less) between the count of the luminescent intensity of the diluted sample and that of the control, the concentration was deemed as "detectable", and the minimum concentration having a significant difference was determined as a limit concentration in the measurement. The results are shown in Table 4.

TABLE 4

| | Present method | | Mono-labeled antibody | |
| --- | --- | --- | --- | --- |
| CEA concentration (ng/ml) | Average value (count) | Standard deviation (count) | Average value (count) | Standard deviation (count) |
| 1.7 | 448719 | 37291.1* | 15927 | 1682.8* |
| 0.17 | 50988 | 4733.7* | 5408 | 552.3 |
| 0.017 | 11267 | 651.9* | 5197 | 690.2 |
| 0.0017 | 7320 | 428.4 | 5310 | 584.9 |
| 0.00017 | 6739 | 411.6 | 5269 | 538.1 |
| 0 | 6774 | 453.4 | 5342 | 622.5 |

*p < 0.01

Table 4 shows that the measurement limit of CEA with the poly-labeled substance of this invention is 0.017 ng/ml, which is by far lower than the limit of 1.7 ng/ml in the measurement of CEA with the mono-labeled substance.

Example 4:
Measurement of Carcinoembryonic Antigen (CEA):
(1) Labeling of an Antibody A labeled anti-CEA antibody was obtained in the same manner as in Example 1 except that Compound 2 obtained in Reference Example 2 was used instead of Compound 1.

(2) Production of Magnetic Particles on Which an Anti-CEA Antibody is Immobilized In 1 ml of a 10 mM phosphate buffer solution (pH 8.0) were dissolved 1 ml of ferrisphere 100A (made by Nippon Paint Co., Ltd.) and 125 μmol of glutaraldehyde, and 100 μl of a 1 mg/ml anti-CEA antibody solution was further added thereto. The mixture was stirred well, and then allowed to stand overnight. The reaction mixture was centrifuged at 3,000 rpm, and the supernatant liquid was taken off through suction. The residue was washed three times with a 10 mM phosphate buffer solution. Subsequently, 500 μl of a 10 mM phosphate buffer solution (pH 8.0) containing 1% BSA and 0.1% $NaN_3$ was added thereto, and the mixture was preserved.

(3) Measurement of CEA

To a polystyrene tube was added 0.5 ml of the solution of magnetic particles on which the anti-CEA antibody was immobilized as produced in (2). Further, 50 μl of standard CEA which was adjusted to 0 to 20.0 ng/ml and 100 μl of the labeled anti-CEA antibody produced in (1) were added thereto. The mixture was incubated at room temperature for 1 hour. The reaction solution was centrifuged at 3,000 rpm, and the supernatant solution was removed by suction. Thereafter, 1 ml of a 10 mM phosphate buffer solution (pH 8.0) containing 0.05% Tween 20 (made by Wako Pure Chemical Industries, Ltd.) was added to the residue as a wash liquid. The mixture was centrifuged, and the supernatant solution was removed by suction. This procedure was repeated three times. A 10 mM acetate buffer solution containing 0.3% hydrogen peroxide and having a pH of 3 was added to the tube, and 200 μl of an aqueous solution containing 0.1M sodium hydroxide was added thereto. Luminescence of the resulting reaction solution was measured by Biolumat LB9500T (manufactured by Berthold). The results are shown in Table 5.

TABLE 5

| CEA concentration (ng/ml) | Present method (count) |
| --- | --- |
| 0 | 4276 |
| 1.0 | 506719 |
| 2.0 | 1009193 |
| 5.0 | 2518382 |
| 10.0 | 5018936 |

Reference Example 1:
(1) Synthesis of an Acrylic Acid Ester Having an Acridine Group Acridine carboxylic acid hydrate (4.6 g, made by Aldrich Chemical Company) was dissolved in 200 ml of dioxane (made by Kanto Kagaku), and 2.4 g of thionyl chloride (made by Kanto Kagaku) was added thereto dropwise. The reaction was carried out at 60° C. for 1 hour. To this was further added 4.4 g of p-hydroquinone (made by Wako Pure Chemical Industries, Ltd.). The reaction was carried out at 60° C. for 5 hours. The reaction solution was concentrated to dryness under reduced pressure, crystallized in toluene (made by Kanto Kagaku), separated by filtration and dried to obtain 5.6 g of hydroquinone ester of acridine carboxylic acid. This ester (3.15 g) and 0.72 g of acrylic acid were dissolved in 200 ml of dioxane, and 2.5 g of dicyclohexylcarbodiimide was dissolved therein. The mixture was reacted at 50° C. for 4 hours. The resulting precipitate was separated by filtration, and the filtrate was concentrated to dryness. The product was then recrystallized from toluene to obtain 2.4 g of acrylic acid ester.

Property value: m.p. 112.6°–113.9° C.

(2) Copolymerization with Maleic Anhydride

One gram of the acrylic acid ester obtained in (i) and 0.2 g of maleic anhydride (made by Aldrich Chemical Company) were dissolved in 100 ml of tetrahydrofuran which was dehydrated well. Nitrogen was introduced into the solution for about 1 hour. As a polymerization initiator, 0.1 ml of a cyclohexane/heptane solution of sec-butyllithium (made by Aldrich Chemical Company) was added dropwise, and the polymerization was started at room temperature. When the viscosity was raised to 200 centipoises, 0.05 ml of isopropanol was added to terminate the polymerization, and Compound (a) was obtained.

(3) Formation of a Maleic Anhydride Block into an N-Hydroxysuccinimide Ester

N-hydroxysuccinimide (0.3 g, made by Kanto Kagaku) was added to a copolymerization solution of Compound (a) obtained in (2), and the mixture was heated as such at 60° C. for 5 hours to obtain Compound (b).

(4) Conversion of an Acridine Group into an Acridinium Group

One ml of methyl trifluoromethanesulfonate (made by Aldrich Chemical Company) was added to a copolymerization solution of Compound (b) obtained in (3). The mixture was stirred and then allowed to stand at room temperature for 24 hours to obtain Compound 1. The obtained polymer was yellow.

Properties; IR, ν $(cm^{-1})$: 2997, 1703, 1500

Reference Example 2:
(1) Synthesis of Acrylic Acid Amide Having an Acridine Group Acridine carboxylic acid hydride (4.6 g, made by Aldrich Chemical Company) was dissolved in 200 ml of dioxane i(made by Kanto Kagaku), and 4.2 g of dicyclohexylcarbodiimide (made by Kanto Kagaku) was added thereto. The reaction was carried out at 50° C. for 1 hour. To this was further added 2.4 g of hexamethylenediamine (made by Wako Pure Chemical Industries, Ltd.). The reaction was carried out at 50° C. for 3 hours. When the liquid became clear, 0.72 g of acrylic acid and 2.5 g of dicyclohexylcarbodiimide were additionally dissolved therein. The reaction was carried out at 50° C. for 4 hours. The resulting precipitate was separated by filtration, and the filtrate was concentrated to dryness. Subsequently, the product was recrystallized from toluene to obtain 3.6 g of acrylic amide.

Properties: m.p. 127°–130° C.

The obtained acrylic amide (2.1 g) was dissolved in 100 ml of dehydrated tetrahydrofuran, and 2 ml of methylsulfonyl chloride (made by Tokyo Kasei) was added thereto. The mixture was heat-refluxed for 2 hours. The reaction solution was concentrated to dryness under reduced pressure, and the product was recrystallized from toluene to obtain 1.56 g of a methylsulfonyl compound.

(2) Copolymerization with Maleic Anhydride

One gram of the methylsulfonyl compound obtained in the above (1) and 0.2 g of maleic anhydride were dissolved in 100 ml of tetrahydrofuran which is dehydrated well, and nitrogen was introduced into the solution for about 1 hour. As a polymerization initiator, 0.1 ml of a cyclohexane/heptane solution of sec-butyllithium was added thereto dropwise, and the polymerization was started at room temperature. When the viscosity was raised to 250 centipoises, 0.05 ml of isopropanol was added to terminate the polymerization, and Compound (c) was obtained.

(3) Conversion of an Acridine Group into an Acridinium Group

One ml of methyl trifluoromethanesulfonate was added to Compound (c) obtained in the above (2). The mixture was stirred, and then allowed to stand overnight to obtain Compound 2. The obtained polymer was yellow, and had a molecular weight of 540,000, as measured by a method for measuring a viscosity via dilution.

Reference Example 3:

Acridine carboxylic acid hydrate (4.6 g, made by Aldrich Chemical Company) was dissolved in 200 ml of dioxane, and 2.4 g of thionyl chloride (made by Kanto Kagaku K.K.) was added thereto dropwise. The reaction was carried out at 60° C. for 1 hour. To this was further added 1.7 g of 4-hydroxybenzylidenemalononitrile (made by Lancaster Co., Ltd.) The reaction was carried out at 60° C. for 5 hours. The solution was concentrated under reduced pressure to 50 ml, crystallized by ice cooling, and separated by filtration to obtain 1.2 g of benzylidenemalononitrile ester of acridine carboxylic acid.

Copolymerization of 1.7 g of this ester with maleic anhydride was carried out in the same manner as described in (2) of Reference Example 1. Then, an acridine group was converted into an acridinium group in the same manner as described in (4) of Reference Example 1 to obtain Compound 6. The obtained polymer had an average weight of 23,000.

Reference Example 4:

The same procedure as described in Reference Example 3 was carried out except for using 1.6 g of 4-hydroxybenzylideneacetone (made by Lancaster Co., Ltd.) instead of 4-hydroxybenzylidenemalononitrile to obtain Compound 7. The obtained polymer had an average weight of 26,000.

Reference Example 5:

Acridine carboxylic acid hydrate (4.6 g, made by Aldrich Chemical Company) was dissolved in 200 ml of dioxane, and 2.4 g of thionyl chloride (made by Kanto Kagaku K.K.) was added thereto dropwise. The reaction was carried out at 60° C. for 1 hour. To this was further added 1.15 g of arylamine and heated at 60° C. for 2 hours. The solution was concentrated under reduced pressure to 50 ml, crystallized by ice cooling, and separated by filtration to obtain 2.2 g of arylamineamide of acridine carboxylic acid.

One gram of arylamineamide of acridine carboxylic acid was suspended in 200 ml of dioxane, and 2 ml of phenylsulfonylchloride was added thereto dropwise until the liquid became clear to synthesize sulfonamide. The solution was concentrated under reduced pressure to 50 ml, crystallized by ice cooling, and separated by filtration. The obtained crystal was copolymerized with maleic anhydride in the same manner as described in (2) of Reference Example 1, and 0.3 g of N-hydrosuccimide was added thereto in the same manner as described in (3) of Reference Example 1. Then, acridine group was converted into an acridinium group in the same manner as described in (4) of Reference Example 1 to obtain Compound 8. The obtained polymer had an average molecular weight of 38,000.

We claim:

1. A method for assaying a ligand in a sample, comprising the steps of:

reacting said ligand in a reaction solution with its specific binding partner, said binding partner being bound to a polyacridinium compound represented by formula (I):

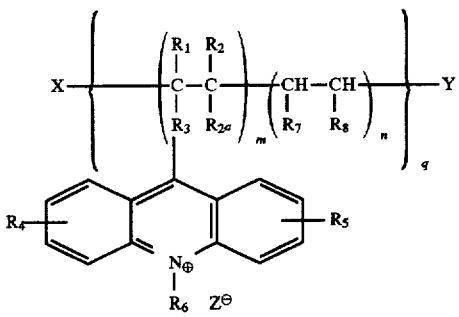

wherein m is an integer of 1 to 10,000, n is an integer of 0 to 10,000, $2 \leq q \leq 20,000$, X denotes hydrogen or a lower alkyl, Y denotes hydrogen, a lower alkyl or a metal, $R_1$, $R_2$ and $R_{2a}$ independently denote hydrogen, a lower alkyl, a lower alkanoyl, optionally substituted aroyl, carboxyl or cyano, $R_3$ is represented by the formula —(COO)$_s$—W—(OCO)$_p$—, —(COO)$_s$—W—N(R$_9$)CO—, —COO—W—W$_a$(N(R$_9$)CO)$_p$—, or —CON(R$_9$)—W—(N(R$_{9a}$)CO)$_p$— (in which W and W$_a$ are different and denote alkylene, optionally substituted phenylene, or optionally substituted naphthylene, R$_9$ and R$_{9a}$ independently denote hydrogen, a lower alkylsulfonyl, or optionally substituted arylsulfonyl, and s and p are independently 0 or 1), $R_4$ and $R_5$ independently denote hydrogen, a lower alkyl, a lower alkoxy, carboxyl or sulfo, $R_6$ denotes optionally substituted lower alkyl, $R_7$ denotes carboxyl, lower alkoxycarbonyl,

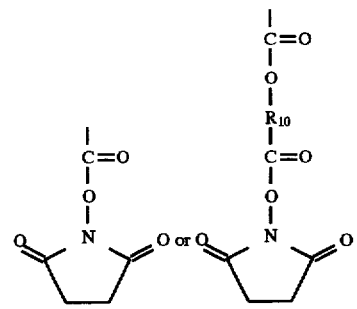

(in which R$_{10}$ denotes alkylene, optionally substituted phenylene, or optionally substituted naphthylene), R$_8$ denotes carboxyl, lower alkoxycarbonyl, optionally substituted lower alkyl, or optionally substituted aryl, or R$_7$ and R$_8$ together form a group represented by the formula

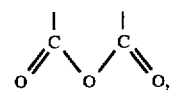

and

Z denotes halogen, methanesufonyloxy or trifluoromethanesulfonyloxy wherein the optional substituent on said optionally substituted aroyl, said optionally substituted aryl, said optionally substituted arylsulfonyl, said optionally substituted phenylene and said optionally substituted naphthylene is 1 to 3 moieties independently selected from the group consisting of lower alkyl, hydroxy, halogen, lower alkoxy, sulfo and carboxyl, and wherein the optional substituent on said optionally substituted lower alkyl is 1 to 3 moieties independently selected from the group consisting of sulfonyl, carboxyl and hydroxyl;

measuring a luminescent intensity of the reaction solution; and correlating said luminescent intensity with the presence or amount of said antigen, antibody or nucleic acid.

* * * * *

UNITED STATES PATENT AND TRADEMARK OFFICE
CERTIFICATE OF CORRECTION

PATENT NO. : 5,665,606

DATED : September 9, 1997

INVENTOR(S) : AKIRA MIIKE

It is certified that error appears in the above-identified patent and that said Letters Patent is hereby corrected as shown below:

COLUMN 1

Line 29, "it" should read --and it--.

COLUMN 2

Line 25, "$R_{2a}$are" should read --$R_{2a}$ are--.

COLUMN 4

Line 7, "group" should read --groups--.

COLUMN 6

Line 46, "N-methylmorphorine" should read --N-methylmorpholine--.

UNITED STATES PATENT AND TRADEMARK OFFICE
CERTIFICATE OF CORRECTION

PATENT NO. : 5,665,606

DATED : September 9, 1997

INVENTOR(S): AKIRA MIIKE

It is certified that error appears in the above-identified patent and that said Letters Patent is hereby corrected as shown below:

COLUMN 7

Line 24, "obtain" should read --to obtain--.

COLUMN 13

Line 67, "compound(Compound" should read
      --compound (Compound--.

COLUMN 14

Line 3, "antiboty," should read --antibody,--.
    Line 4, "antibody" should read --antibodies--.
    Line 5, "Compound 6," should read --Compounds 6,--.
    Table 2, "Monolabeled" should read --Mono-labeled--.

COLUMN 16

Line 8, "(i)" should read --(1)--.
    Line 33, "Properties;" should read --Properties:--.
    Line 39, "i(made" should read --(made--.

UNITED STATES PATENT AND TRADEMARK OFFICE
CERTIFICATE OF CORRECTION

PATENT NO. : 5,665,606

DATED : September 9, 1997

INVENTOR(S) : AKIRA MIIKE

It is certified that error appears in the above-identified patent and that said Letters Patent is hereby corrected as shown below:

<u>COLUMN 18</u>

Line 25, "$W_a$" should read --$W_a$--.
Line 64, "methanesufonyloxy" should read
   --methanesulfonyloxy--.

Signed and Sealed this

Eleventh Day of August 1998

Attest:

BRUCE LEHMAN

Attesting Officer    Commissioner of Patents and Trademarks